(12) United States Patent
Finarov

(10) Patent No.: US 7,289,234 B2
(45) Date of Patent: Oct. 30, 2007

(54) METHOD AND SYSTEM FOR THIN FILM CHARACTERIZATION

(75) Inventor: Moshe Finarov, Rehovot (IL)

(73) Assignee: Nova Measuring Instruments Ltd., Rehovot (IL)

( * ) Notice: Subject to any disclaimer, the term of this patent is extended or adjusted under 35 U.S.C. 154(b) by 0 days.

(21) Appl. No.: 11/389,297

(22) Filed: Mar. 27, 2006

(65) Prior Publication Data

US 2006/0176494 A1    Aug. 10, 2006

Related U.S. Application Data

(63) Continuation of application No. 10/259,828, filed on Sep. 30, 2002, now Pat. No. 7,019,850.

(30) Foreign Application Priority Data

Sep. 30, 2001    (IL)  ..................................... 145699

(51) Int. Cl.
    *G01B 11/28*    (2006.01)
(52) U.S. Cl. ..................... 356/630; 356/237.2
(58) Field of Classification Search ................. 356/630, 356/237.2–237.5, 239.3, 239.7, 625–629, 356/601; 250/559.27, 372
    See application file for complete search history.

(56) References Cited

U.S. PATENT DOCUMENTS

| 4,899,055 | A  | 2/1990  | Adams |
|-----------|----|---------|-------|
| 4,999,508 | A  | 3/1991  | Hyakumura |
| 5,517,312 | A  | 5/1996  | Finarov |
| 5,682,242 | A  | 10/1997 | Eylon |
| 5,867,590 | A  | 2/1999  | Eylon |
| 5,872,633 | A  | 2/1999  | Holzapfel et al. |
| 5,883,720 | A  | 3/1999  | Akiyama et al. |
| 6,406,641 | B1 | 6/2002  | Golzarian |
| 6,570,662 | B1 | 5/2003  | Schietinger et al. |
| 6,841,224 | B2 | 1/2005  | Kamata et al. |

OTHER PUBLICATIONS

L. Ward, *The Optical Constants of Bulk Materials and Films*, Philadelphia: Institute of Physics Publishing, pp. 167-180, Oct. 1994.

*Primary Examiner*—Layla G. Lauchman
(74) *Attorney, Agent, or Firm*—Browdy and Neimark, PLLC

(57) ABSTRACT

A method and system are presented for optical measurements in multi-layer structures to determine the properties of at least some of the layers. The structure is patterned by removing layer materials within a measurement site of the structure from the top layer to the lowermost layer of interests. Optical measurements are sequentially applied to the layers, by illuminating a measurement area in the layer under measurements, when the layer material above said layer under measurements is removed, thereby obtaining measured data portions for the at least some of the layers, respectively. The properties of each of the at least some layers are calculated, by analyzing the measured data portion of the lowermost layer, and then sequentially interpreting the measured data portions of all the other layers towards the uppermost layer, while utilizing for each layer the calculation results of the one or more underlying layers.

33 Claims, 5 Drawing Sheets

METHOD AND SYSTEM FOR THIN FILM CHARACTERIZATION

FIELD OF THE INVENTION

This invention is generally in the field of optical measurement techniques, and relates to a method and system for thin film characterization in multi-layer structures (film stack). The invention is particularly useful in the manufacture of semiconductor devices.

BACKGROUND OF THE INVENTION

A semiconductor wafer typically presents a patterned structure, wherein the pattern is in the form of multiple-layer stacks. Various steps in the manufacture of semiconductor devices require measurements of thickness and/or other characteristics of each layer in the semiconductor wafer. NovaScan machines commercially available from Nova Measuring Instruments Ltd. utilize spectrophotometric thickness measurements applied to predetermined sites on the wafer, each containing a known layer stack described by a predefined optical model based on optical properties of all the stack layers.

It is especially important to determine the optical properties of each layer (film) of the actual stack resulting from the mandating steps and before performing further measurements such as measurement of the uppermost layer thickness, etc. Unfortunately, in cases when measurements are performed on the entire stack, the accurate determination of the properties of eat separate layer is difficult to implement, and in some cases, even impossible, because of too many independent parameters to be involved, and thus causing uncertainty in data interpretation. In order to exclude such uncertainty, usually each unknown layer is separated by its deposition on a known substrate without other layers of the multi-layer stack and measured independently. However, the properties of the individually deposited layer may be different from those of the similar layer that passes all processing steps during the manufacture of a required multi-level stack.

SUMMARY OF THE INVENTION

There is accordingly a need in the art to facilitate thin film characterization of individual film layer/layers within actual entire multi-film stack, by providing a novel system and method.

According to one aspect of the present invention, there is provided a method of optical measurement in multi-layer sues to determine the properties of at least some of the layers, the method comprising:

(i) patterning the structure by removing layer materials within a measurement site of the structure from the top layer to the lowermost layer of interest;

(ii) applying optical measurements to measurement areas of said at least some of the layers, with the layer materials above the area sneer measurements being removed, thereby obtaining measured data portions for said at least some of the layers, respectively;

(iii) calculating the properties of each of said at least some layers, by analyzing the is measured data portion of the lowermost layer, and then sequentially interpreting the measured data portions of all the other layers from said at least some layers towards the uppermost layer, while utilizing for each layer the calculation results of the one or more underlying layers.

It should be understood that the term "lowermost layer" used herein refers to the lowermost layer from the layers to be measured, and is not necessarily the actual lowermost layer in the stack.

The patterning may include formation of a cross-section in the structure having a slope-like profile. In this case, the optical measurements are sequentially applied to said at least some of the layers in the patterned structure. The optical measurements for each layer preferably include measurements in several points of the layer along the respective slope region. The sequential measurements may be started from the lowermost layer. The calculation and the data interpretation cycle with respect to each layer from said at least some layers may be carried out prior to or concurrently with applying measurements to the next upper layer, or upon applying the optical measurements sequentially to all the layers of interest. The optical measurements may be first applied to the uppermost layer. In this case, the calculation and the data interpretation cycles with respect to each layer are carried out upon applying the optical measurements sequentially to all the layers of interest.

The formation of the slope profile may be performed by polishing, e.g., chemical mechanical polishing. The formation of the slope profile may be performed by etching, e.g., by a focused ion beam.

The patterning may be done by the sequential removal of the layers materials from the uppermost layer to the lowermost one, and the optical measurements may be sequentially applied to the layers starting from the uppermost layer, such that each layer is measured with no layer material above said layer. In this case, the patterning may be performed by ion beam bombardment.

The optical measurements may include one of the following: spectrophotometric measurements, ellipsometry measurements, FTIR based measurements, scatterometic measurements. The measurements may utilize polarized light. The optical measurements may utilize collection of specularly reflected light.

The layer properties to be determined include at least one of the following: refractive index (e.g., as a function of wavelength of incident light e.g., between DUV and NIR range), extinction coefficient (e.g., as a function of wavelength of incident light, e.g., between DUV and NIR range), and layer thickness.

According to another aspect of the present invention, there is provided, a system for optical measurements in multi-layer structures to determine the properties of at least some of the layers, the system comprising:

(a) a layer material removing unit operable to remove layer materials within a measurement site of the structure from the top layer to the lowermost layer of interest, thereby crew a pattern in the structure;

(b) an optical measuring unit coming an illuminator, a light directing optics and a detection unit, and operable to sequentially apply optical measurements to each of the measured layers when the layer mater above said measured layer is removed and generating measured data portion indicative of detected light;

(c) a data processor system operable to calculate the properties of each of said at least some layers, by analyzing the measured data portion of the lowermost layer, and then sequentially interpreting the measured data portions of all the other layers from said at least some layers towards the uppermost layer, while utilizing for each layer the calculation results of the one or more underlying layers.

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF THE INVENTION

Figure 1:
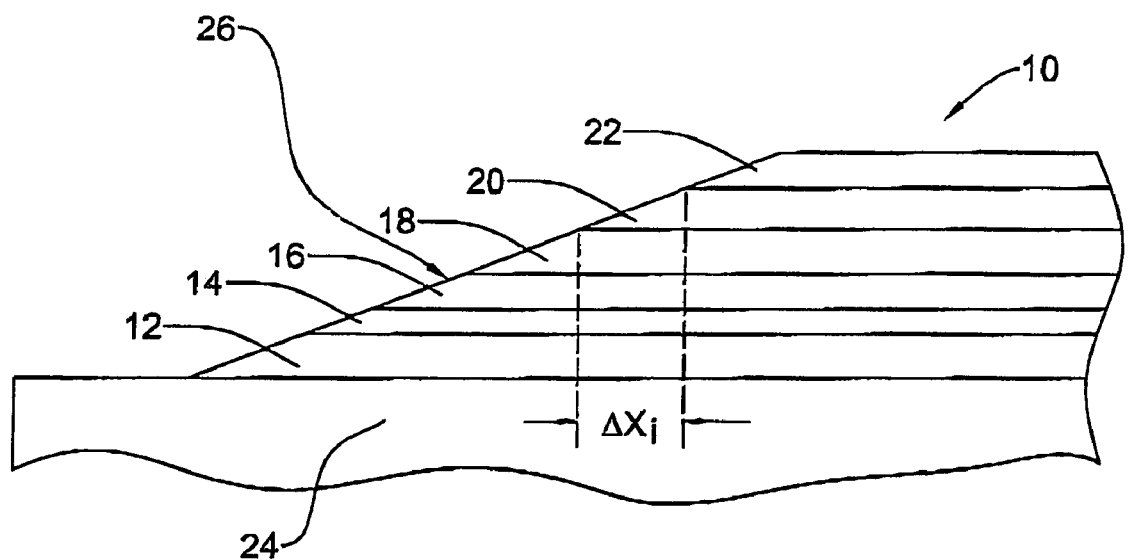
FIG. 1 schematically illustrates a cross-sectional view of a multi-layer structure, such as a semiconductor wafer, specifically processed to define a measurement slope thereon for the purposes of the present invention.

Referring to FIG. 1 there is illustrated a partial cross-sectional view of a multi-layer sure 10, e.g., a semiconductor wafer, whose parameters are to be measured. The structure 10 is formed of a plurality of layers, six layers 12-22 in the present example, on top of a substrate 24. In the example of FIG. 1, the structure is processed to define a measurement slope 26. The slope 26 (cross-section) is formed in the surface of the structure 10 in a such manner that the structure thickness along the slope varies from zero, i.e. from the bottom of the lowermost layer within the slope area, up to the maximal value, i.e., the top of the uppermost layer of the structure. It should be understood that practically, the bottom of the lowermost layer within the slope is the top of the substrate, but generally, may be the top of an intermediate layer, provided one or more underneath layers affect the reflection from the lowermost layer in the known manner.

In the example of FIG. 1, the slope profile is substantially flat forming a certain angle with the substrate plane. It should, however be understood that the slope profile may alternatively be curved, depending on the technique of its fabrication.

Figure 2:
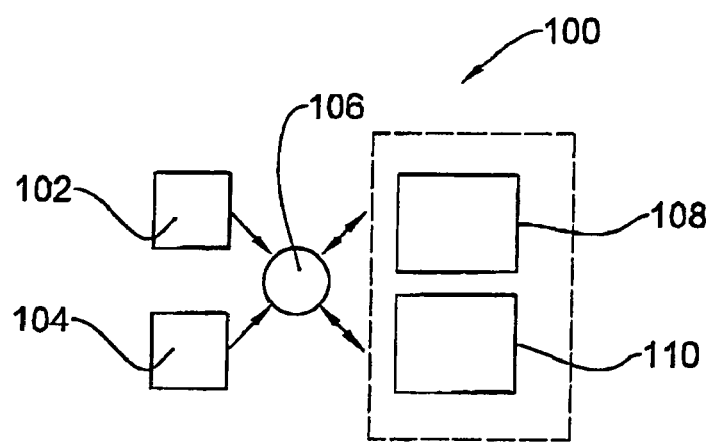
FIG. 2 schematically illustrates a system according to one embodiment of the invention for measuring the optical characteristics of multi-layer structures.

FIG. 2 schematically illustrates a system 100 according to on embodiment of the invention for thin film measurements in a multi-film (multi-layer) structure. The system 100 is the so-called "combined measurement tool". The combined measurement tool 100 comprises a slope (cross-section) forming unit 108 and an optical measuring system 110. For the specific application of measuring in semiconductor wafers, the system 100 is associated with input and output cassettes 102 and 104, and an internal wafer transferring unit 106, e.g. robot. The transferring unit 106 transfers a wafer from input cassette 102 to the slope forming unit 108, then transfers the wafer-with-slope to the optical measuring system 110, and then returns the measured wafer into the output cassette 104. The slope forming unit 108 is appropriately designed to form the slope using any known suitable technique (as will be described below) on the multi-layer structure, preferably prepared in a test site on the wafer. The optical measuring system 110 is of the kind capable of measuring the thickness or other characteristics of each of the layers in the stack, as will be exemplified below with reference to FIG. 3.

The system 100 is connectable to a processor unit (not shown) installed with suitable hardware and software utilities performing fully automated control of the slope formation procedure, wafer transfer, and optical measurements of the thickness and other optical characteristics of each layer of the stack. The processor is provided with user interface and is connectable to the FAB computer network or specific processing tool that utilizes measured data for further process control or for other purposes.

Figure 3:
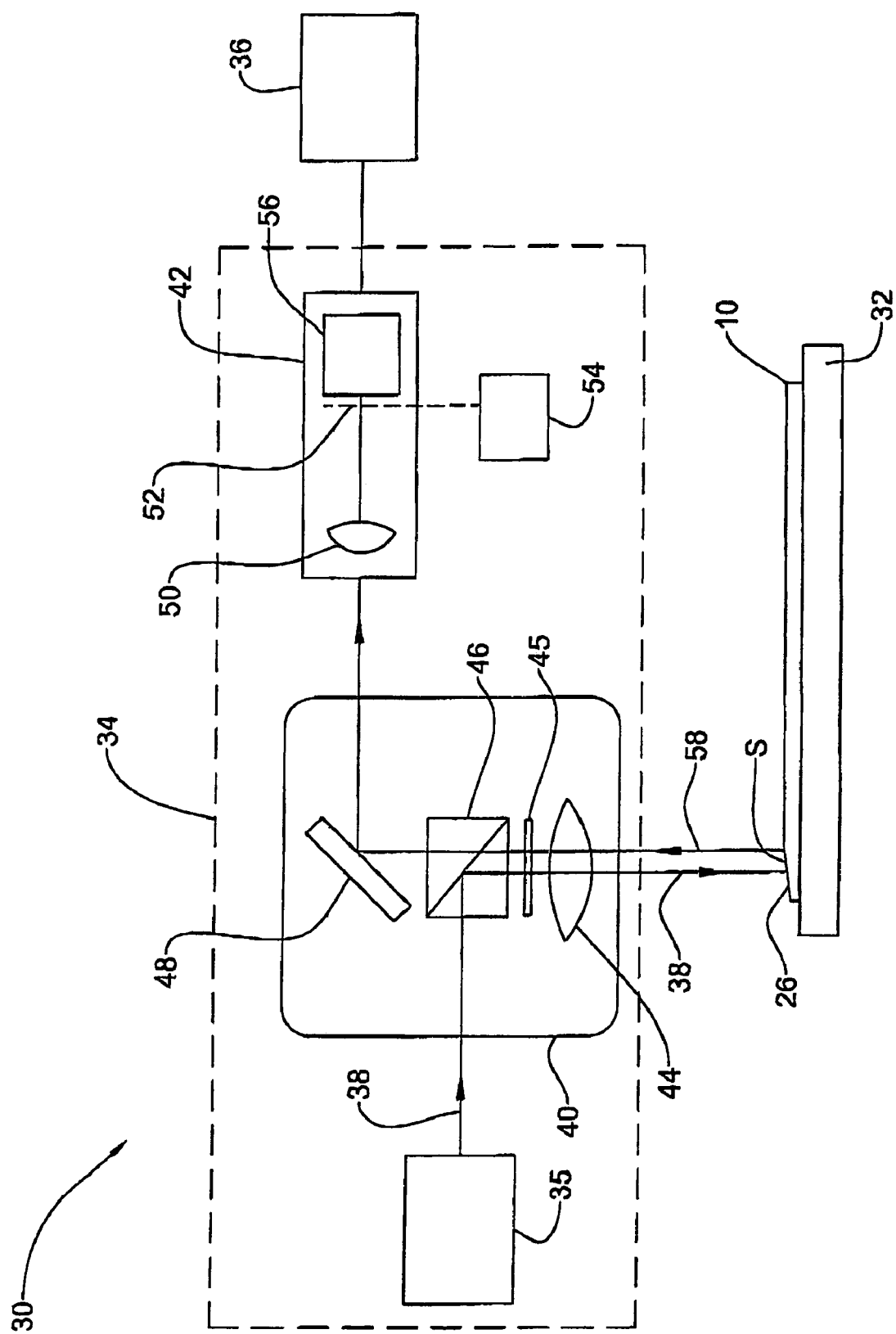
FIG. 3 schematically illustrates an optical measurement apparatus suitable for use in the system of the present invention.

Reference is now made to FIG. 3 exemplifying the construction and operation of the optical measuring system 110 suitable. The system 110 comprises a support frame 32 for holding the structure 10 within an inspection plane, a spectrophotometer apparatus 34, and a processor unit 36 connectable to the spectrophotometer. The spectrophotometer apparatus 34 typically includes a light source 35 for producing a light beam 38 of a predetermined broad wavelength range (preferably between DUV and NIR), light directing optics 40, and a detector unit 42. The light directing optics 40 includes an objective lens 44 and a beam splitter 46, and optionally includes light deflector (mirror) 48. The detector unit 42 includes a tube lens 50, a variable field stop 52 operable by a motor 54, and a spectrophotometric detector 56. Optionally provided in the system 110 is a polarizer 45 that is preferably rotatable to enable measurements of spectral reflectance for at least two different polarizations of light.

The construction and operation of the spectrophotometer apparatus 34 may be also of any known kind, for example, such as disclosed in U.S. Pat. No. 5,517,312 assigned to the assignee of the present application, and therefore need not be specifically described, except to note the following. The incident light beam 38 passes through the light directing optics 40 and impinges onto the structure 10 at a certain location on the slope 26 defining a measurement area S. Light component 58 is specularly reflected from reflective regions within the measurement area S along the same optical axis as beam 38 (on FIG. 3 they are separated for illustration only) and directed onto the detector unit 42. By providing a relative displacement between the wafer and the optical axis of the light directing optics within a plane parallel to the inspection plane, a plurality of areas along the slope are measured.

It should be noted that generally, the illuminated location on the structure may be larger than the actual measurement area S, in which case suitable optics (e.g., one or more apertures in the optical path of the reflected light collected by the objective lens) is provided for capturing light reflected solely from the part (area S) of the illuminated location. In other words, the measurement area (region of interest) is included into a spot-size provided by the incident light beam 38 on the structure 10.

In order to facilitate understanding of the system operation, the illuminated area defined by the diameter of the incident beam 38 is assumed as constituting the measurement area S. The diameter of the field stop 52 may be variable and is set automatically according to the desired size of the measurement area. Turning back to FIG. 1, the diameter of the incident beam 38 defining the measurement area S, is preferably significantly smaller than the layer cross-section $\Delta_{x_i}$ within the slope (i.e., $S_1 \ll \Delta_{x_i}$), in order to ensure the maximal thickness uniformity of the layer within the measurement spot.

For example, if a typical layer thickness is 1000 Å, a required thickness uniformity is 10 Å, and the spot size S is about 10 μm, the cross-section length $\Delta_{x_i}$ of this layer should be about 1 mm (10 μm×1000 Å/10 Å). In his case, it is possible to perform measurements in 100 (1 mm/10 μ) non-overlapped points along the slope. Multiple-point measurements of each layer, when the only variable is the layer thickness, allow the determination of the layer optical properties, i.e. index of refraction n and extinction coefficient k as function of wavelength, with very high accuracy. Hence, in any point i of the measurement slope, three independent parameters—thickness $d_i$, refraction index $n_i$ and extinction coefficient $k_i$ may be measured.

A way of verification of the measurement results (measured data) is a function d=f(x) (wherein d is the layer thickness and x is the coordinate along the same direction) that should comply with the measurement slope line, e.g. linear function or any other known function. When the measurement slope has a well-known form, a value of the layer's thickness may be calculated from this function and only values of n and k may be calculated form the optical measurements.

The optical measurements are applied consequently by moving the measurement spot along the measurement slope from the bottom of lowermost layer (substrate surface) up to the top layer. Optical constants calculated for underlying layers are used consequently for calculations of the optical parameters of the next upper layer.

The processor unit 36 may also comprise pattern recognition software and translation utilities which, in combination with a suitable detector such as a CCD camera, provide an optical alignment of the wafer and allows for locating the measurement site area. Alignment techniques suitable to be used in the present invention may be of the kind based on scribe lines or asymmetrical features within the die, for example as disclosed in U.S. Pat. Nos. 5,682,242 and 5,867,590, assigned to the assignee of the present application.

Figure 4:
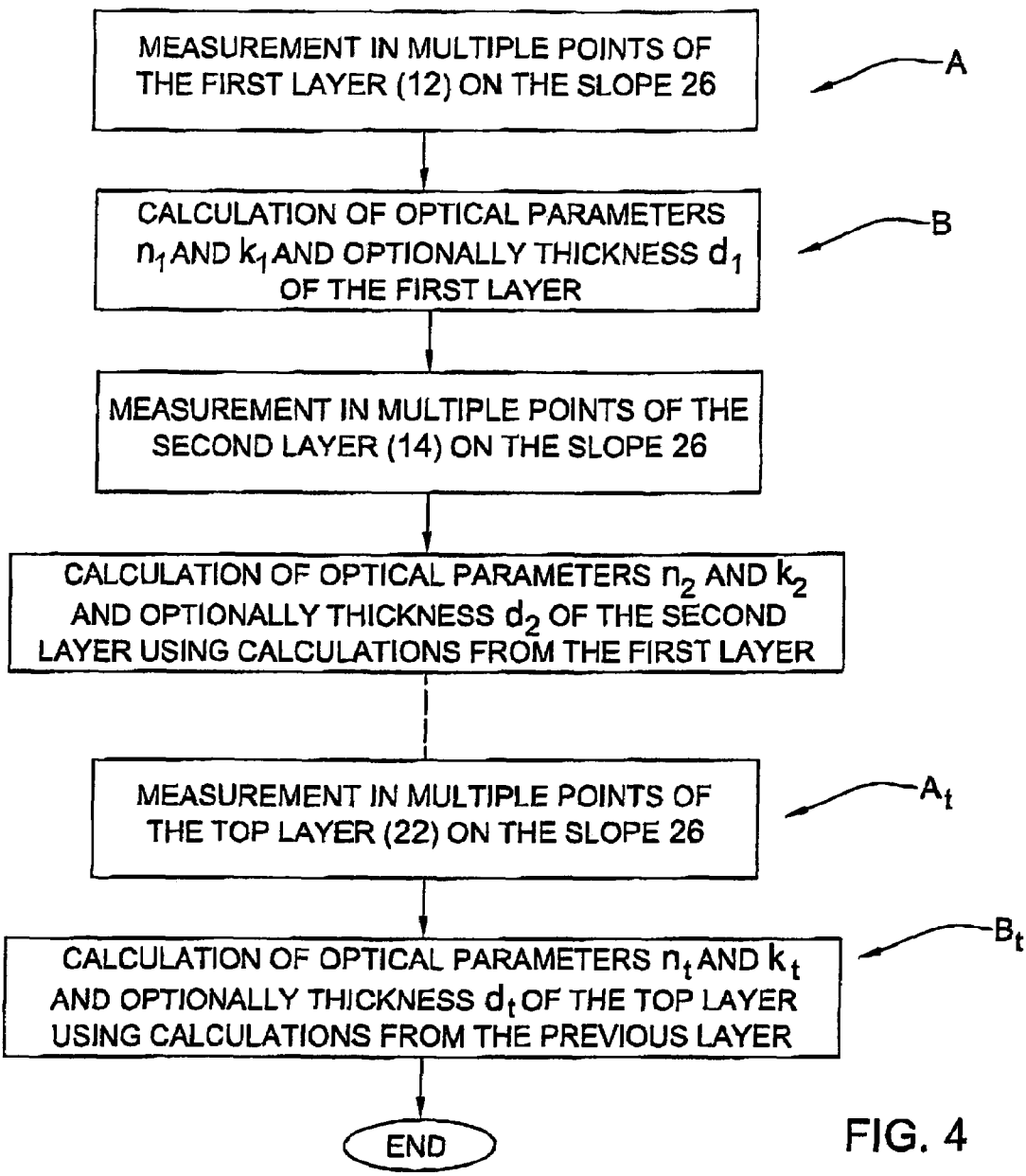
FIG. 4 exemplifies a flow diagram of the method according to the invention.

The main principles of a method according to the invention will now be described with reference to FIG. 4. Measurements are first applied to multiple points of the lowermost layer (layer 12 in the preset example of FIG. 1) within the slope region. This is implemented by movement of the measurement spot along the slope (e.g., by moving the stage with respect to the optical a of the light directing optics). Light components reflected from the measurement areas are successively detected, and the measured data is obtained (measurement step A), e.g., in the form of photometric intensities of each wavelength for both polarizations of light $R_p(\lambda)$ and $R_s(\lambda)$ (or for non-polarized light—R(λ)) within the wavelength range of the incident radiation. Concurrently, the processor (36 in FIG. 3) calculates the optical parameters $n_1$ and $k_1$ of the first (lowermost) layer, and optionally also the thickness $d_1$ of this layer, from the photometric intensities of the reflected light (data interpretation step B). Upon reaching the bottom plane of the second layer (layer 14 in FIG. 1), steps A and B are repeated with respect to the second layer, while utilizing in the optical model of two-layer stack the previously obtained optical constants of the first layer. In such a manner, measurement and data interpretation steps A and B are performed consequently for all the layers in the stack.

More specifically, the data interpretation stop B may contain the following stages:

Measured data, e.g. in the form of optical functions presenting photometric intensities of each wavelength for both linear polarizations of light $R_p(\lambda)$ and $R_s(\lambda)$, obtained in q points along the layer cross-section within the slope region is analyzed, and parameters n(λ), k(λ) and d are calculated. It should be noted that for normal incidence mode, $R_p(\lambda)=R_s(\lambda)$.

Various different approaches for expressing the optical functions of a thin film in terms of the optical parameters, layer thickness and the angle of light incidence can be used, for example as disclosed in "The Optical Constants of Bulk Materials and Films", L. Ward, pp, 167-180. Such approaches and their applications are known per se and therefore need not be specifically described. Both n and k are functions of the wavelength of light, i.e., they have dispersion and may be presented in different ways. The most applicable expression of optical functions is the Cauchy approximation, that presents n- and k-dispersion in a polynomial form:

$$n(\lambda)=A_n+B_n/n^2+C_n/n^4 \qquad (1)$$

$$k(\lambda)=A_k+B_k/k^2+C_k/k^4 \qquad (2),$$

wherein $A_n$, $B_n$, $C_n$, $A_k$, $B_k$ and $C_k$ are independent parameters.

Thus, for each layer, six independent Cauchy parameters ($A_n$, $B_n$, $C_n$, $A_k$, $B_k$ and $C_k$) for n and k should be calculated. An additional variable parameter for each measurement (in each point) is the thickness d of the layer along the slope.

Thus, for each q-th measurement there are six Cauhcy parameters ($A_n$, $B_n$, $C_n$, $A_k$, $B_k$ and $C_k$) and one individual parameter d to be found. In order to enable determination of the entire set of optical parameters with a high level of confidence, generally more than six independent measurements should be applied. Thus, more than seven points (q>7) along the slope region of each layer are preferably measured. In many cases, e.g., in a structure containing parent dielectric films (i.e. $A_k=B_k=C_k=0$), the number of variables may be less than 7.

The above-described technique enables measurements in fully automated mode, including positioning the measurement spot on the measurement slope (cross-section), optical measurements at each point along the slope, and calculation of the optical parameters of each layer of the stack. It should be noted, that other than Cauchy functions of optical dispersion may be used. The number of unknowns to be calculated should correspond to the number of measured points along the slope within the measured layer.

After completing the measurements of the first layer and calculating its optical parameters n(λ) and k(λ), the same procedure is successively repeated on the second and all further layers until the measurements in the last (top) layer are completed. This concept is based on the utilization of the optical parameters of the underlying layer(s) as constants in the calculation of the optical parameters of each specific layer, and thus only the optical parameters of the measured upper layer need to be calculated.

It should be noted that the above technique can be used with any suitable measurement technique for measuring the layer parameters. Spectrophotometric measurements exemplified above can be replaced by any other measuring technique, e.g. ellipsometry (spectral or monochromatic), FTIR (Fourier Transform Infra-Red), scatterometry and any other optical method that measures characteristics of the entire multi-layer stack depending on the individual properties of each layer.

The measurement slope (cross-section) on the structure to be measured may be prepared using different techniques. For example, a mechanical polishing process could be applied to the multi-layer structure (e.g., semiconductor wafer). In this case, the wafer may be handled slightly inclined with respect to a polishing cylinder and moved during the polishing with a speed providing the desired slope of the cross-section, or may be handled horizontally and moved with a variable speed relative to a polishing cylinder pressed against the wafer's surface. In an alternative example, a polishing pad of spherical or cylindrical shape may be used, in which case a measurement slope in the form of a spherical or arch-shaped recess is formed in the surface of a static wafer, with the bottom part reaching the lowermost layer (e.g., substrate (Si) of the wafer structure).

Different chemical, physical or combined material removal techniques (e.g., etching) could also be applied to form the measurement slope (cross-section). For example, the so-called "focused ion beam" (FIB) etching technique can be used. In this case, an ion generating device directs a focused ion beam to the wafer's surface, and the ion beam start milling (anisotropically etching) a small area on the surface of the wafer. By providing the relative movement of the wafer and the ion beam with a variable speed, a slope-like (cross-section) profile is formed within the structure. Other configurations of the FIB could be used (rather than moving the wafer), e.g. oblique ion beam, defocused ion beam, etc. Also, chemical assisted ion etching may be used along with a Focused Ion Beam (FIB). This technology allows for simplifying and decreasing the size of the combined measurement tool, which is critical for clean room environment in the manufacture of semiconductor devices.

Figure 5:
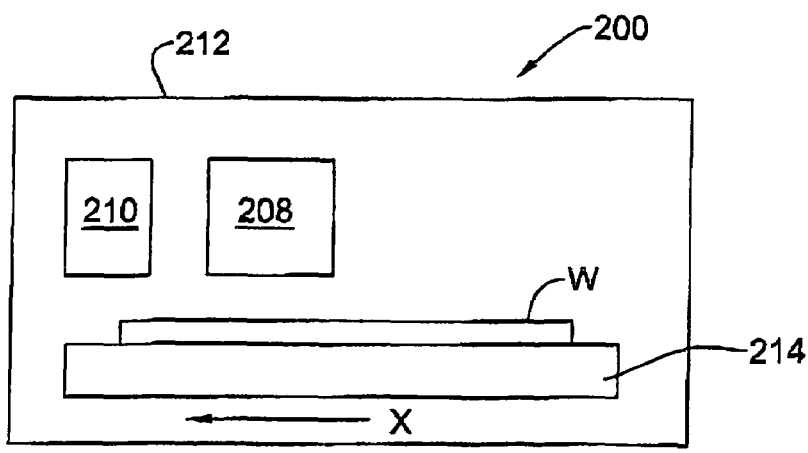
FIG. 5 schematically illustrates a system according to another embodiment of the invention for measuring the optical characteristics of multi-layer structures.

Reference is now made to FIG. 5, schematically illustrating a combined measurement tool 200 accord to another embodiment of the invention. The measurement tool 200 is generally similar to that of FIG. 2 (i.e., is associated with input and output cassettes and an internal wafer transferring means), but differs in that a slope forming unit 208 and optical measuring system 210 are located within a common vacuum chamber 212. Additionally, in order to decrease the entire system's size, a common movable stage 214 for slope forming unit 208 and the optical measuring system 210 can be used. The stage 214 provides handling of a wafer W and movement thereof along the X-axis for the purposes of forming the measurement slope and performing the measurement along the slope.

In the above-described examples, the thin film characterization was carried out by manufacturing a cross-section of a very small slope and measuring optical parameters along this cross-section, so that for each layer there are several measuring points on the cross-section corresponding to different thicknesses of the layer. The determination of the n and k values for each layer is performed by the data interpretation starting from the lowermost layer for each next point, so that for each top measured point, the underlying layer(s) are determined as previous steps and are considered as known.

The method of slope cross-section is simple in implementation. However, since it requires a significant size at least in one dimension (about 10 mm in length), the method might be inapplicable for patterned structures where areas of interest (features in wafer) are about 2 orders of magnitude smaller. For example, considering a pad of about 50 μm×50 μm in size that is a stack of several layers to be measured, the method of material characterization has to allow access to each layer in several values (points) of thickness with a light spot less than the pad size and without interaction of the surrounding areas that may have different layer structures. In other words, optical parameters are to be measured within the selected area (pad, test site, feature) in parallel to removing the material of this specific stack. One of the most applicable methods of material removal suitable in this specific case, is ion milling that allows the removal of very thin layers of practically any material, by bombarding the surface of a structure with accelerated ions, e.g., argon.

Figure 6A:
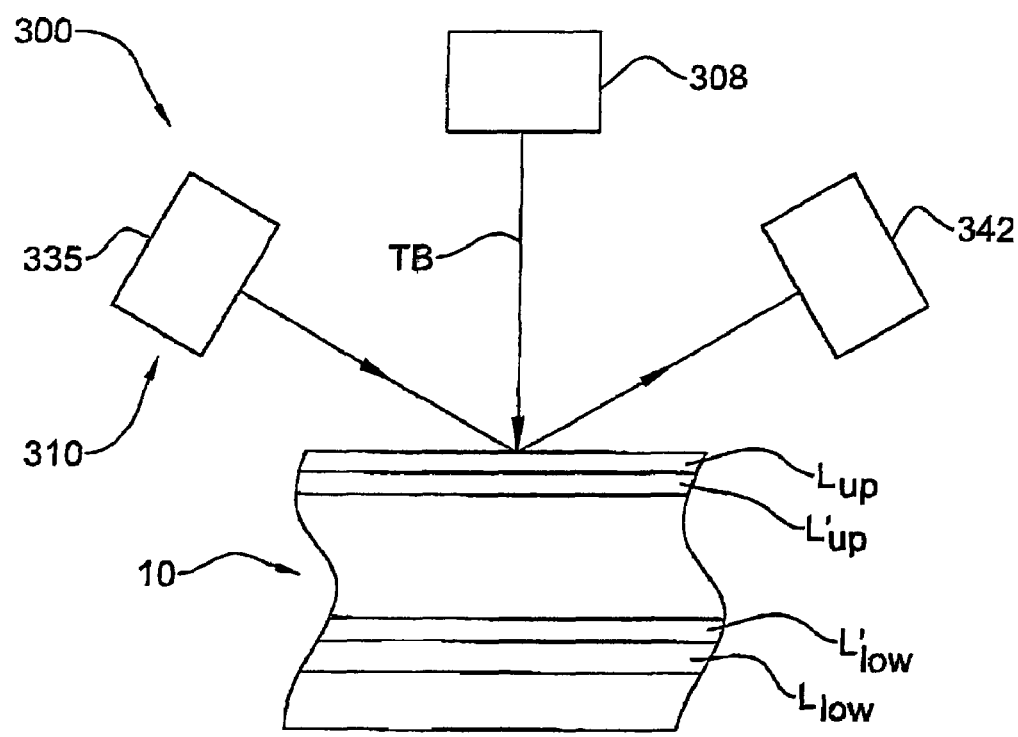
FIGS. 6A and 6B illustrate two more embodiments of the system according to the invention.
Figure 6B:
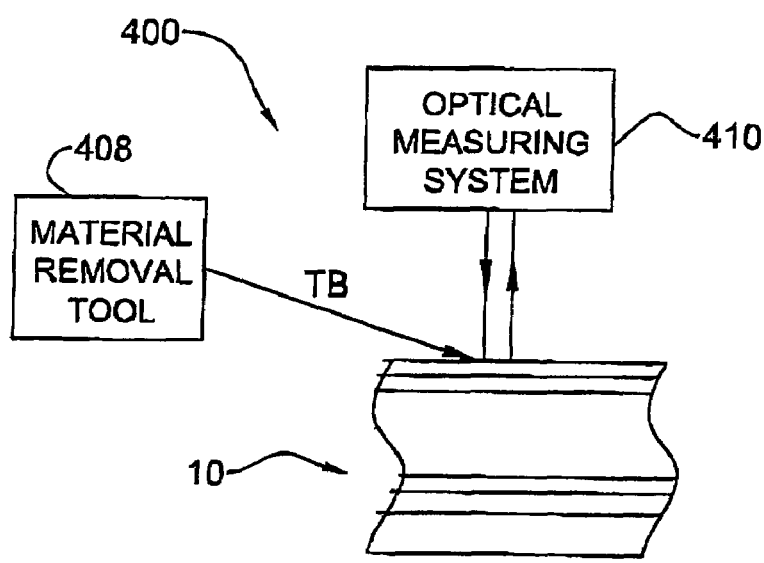

The above concept of substantially concurrent material removal (slope formation) and optical measurements is exemplified in FIGS. 6A and 6B. In these examples, the material removal is sequentially applied to all the layers starting from the upper layer and continuing downwards to the lowermost layer of interest, while concurrently applying measurements to the layers from the upper layer underneath the removed one to the lower layer.

In the example of FIG. 6A, a combined slope formation and measurement tool 300 has an optical measuring system 310, which, while operating in specular reflection mode, utilizes oblique incidence instead of normal incidence of light onto the structure, thus leaving a space for a material removal tool 308, which normally directs an ion beam onto the structure. The optical measuring system 310 typically includes a light source 335 for producing a light beam of a predetermined broad wavelength range (preferably between DUV and NIR), light directing optics (not shown), and a detector unit 342. The optical measuring system 310 operates to apply measurement to the entire structure 10 via illumination of the uppermost layer $L_{up}$. Then, the ion beam IB successively removes the layers from the uppermost layer $L_{up}$ to the lowermost layer $L_{low}$, and the optical measuring system 310 operates to successively direct an incident beam 38 to illuminate measurement areas in the layers and collect specularly reflected light 58, staring from the measurement area in a layer $L'_{up}$ underneath the uppermost layer immediately after the removal of the layer portion $L_{up}$, and so on, until the lowermost layer $L_{low}$ to which measurements are applied immediately after the ion beam removal of the layer portion $L'_{low}$ above the layer $L_{low}$.

In the example of FIG. 6B, a combined material removal and measurement tool 400 is designed such that a material removal tool 408 directs an ion beam IB to the structure at a certain angle, while an optical measuring system 410 operates in a specular reflection mode, similarly to that of FIG. 3.

Figure 7:
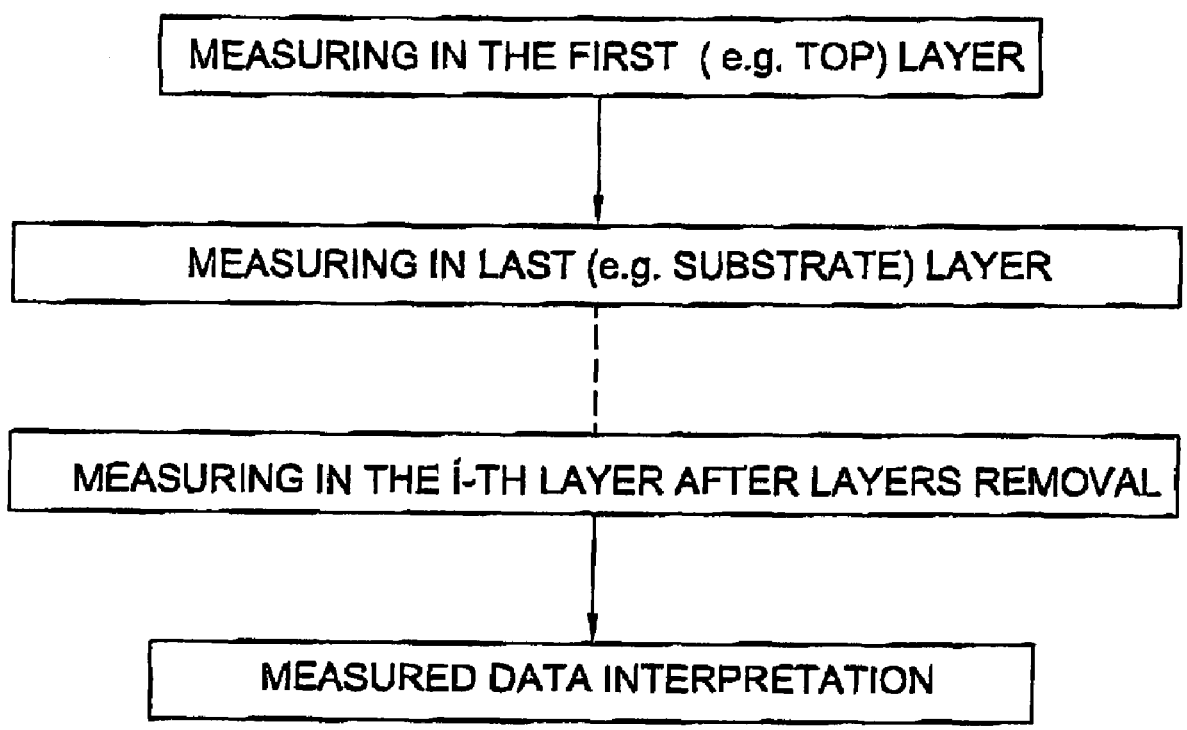
FIG. 7 exemplifies a flow diagram of the method according to the invention.

Generally, there are a number of measurements, each corresponding to different stack thickness, from the top surface and downwards to the lowermost surface (e.g., substrate). Data interpretation is applied to the measured data after collecting measurements from all the layers. It should be understood that the method of the present invention in any one of the above-described system configurations, can consist of first sequentially applying measurements to all the layers (staring either from the lowermost layer or from the uppermost layer) and then carrying out data interpretation steps. This is illustrated in FIG. 7. Measurements are applied to the first layer, which may be tie uppermost layer, in which case measurements can be applied prior to layer removal or after the formation of the entire slope. Then measurements are sequentially applied to i layers in the stack and i portions of measured data are obtained. This can be implemented upon creating the entire slope or concurrently with the layer removal. There the measured data is interpreted in appropriate cycles staring from the lowermost layer (e.g. substrate).

Those skilled in the art will readily appreciate that many modifications and changes may be applied to the invention as hereinbefore exemplified without departing from its scope, as defined in and by the appended claims. In the method claims, which follow, characters that are used to designate claim steps are provided for convenience only, and do not apply to any particular order of performing the steps.

The invention claimed is:

1. Method of optical measurements of thin film structures for determining the properties of at least one thin film, the method comprising:
   (i) applying at least partial material removal of said at least one thin film of the structure thereby forming measurement areas with different material thickness;
   (ii) performing optical measurements on at least some of said measurement areas, thereby obtaining measured data portions for said at least some of the measurement areas with different material thickness, respectively;
   (iii) determining the properties of said at least one thin film, by analyzing the measured data portion of the measurement area with minimal material thickness, and then sequentially interpreting the other measured data portions of the other measurement areas from the measured data portion of the measurement area with minimal material thickness towards the measured data portion of the measurement area with maximal material thickness, while utilizing for each measurement area the calculation results for the one or more measurement areas with smaller material thickness.

2. The method according to claim 1, wherein said at least partial material removal includes formation of a cross-section in the structure having a slope-like profile.

3. The method according to claim 2, wherein the optical measurements are sequentially performed on said at least some of measurement areas with different material thickness.

4. The method according to claim 3, wherein the optical measurements are first performed on the measurement area with smaller material thickness.

5. The method according to claim 4, wherein the determination of the properties of said at least one thin film and cycles of the data interpretation with respect to each measurement area is carried out prior to or concurrently with performing the optical measurements on the next measurement area.

6. The method according to claim 4, wherein the determination of the properties of said at least one thin film and cycles of the data interpretation with respect to each measurement area are carried out upon performing the optical measurements sequentially to all the measurement areas.

7. The method according to claim 2, wherein the formation of the slope profile comprises polishing.

8. The method according to claim 7, wherein said polishing includes chemical mechanical polishing.

9. The method according to claim 2, wherein the formation of the slope profile comprises etching.

10. The method according to claim 9, wherein said etching utilizes a focused ion beam.

11. The method according to claim 1, wherein said at least partial material removal includes sequential removal of the thin film material from said structure, and the optical measurements are sequentially performed on said at least some measurement areas with different material thickness.

12. The method according to claim 11, wherein said at least partial material removal comprises ion beam bombardment.

13. The method according to claim 1, wherein said optical measurements include one of the following: spectrophotometric measurements, ellipsometry measurements, FTIR based measurements, scatterometric measurements.

14. The method according to claim 13, wherein the spectrophotometric measurements utilize polarized light.

15. The method according to claim 1, wherein the film properties include at least one of the following: refractive index, extinction coefficient and layer thickness.

16. The method according to claim 15, comprising determining the refractive index as a function of wavelength of incident light.

17. The method according to claim 15, comprising determining the extinction coefficient as a function of wavelength of incident light.

18. The method according to claim 13, wherein said optical measurements comprise illuminating the structure with incident light of a wavelength range between DUV and NIR ranges.

19. The method according to claim 1, wherein the optical measurements utilize collection of specularly reflected light from the structure.

20. Method of optical measurements of thin film structures for determining the properties of at least one thin film, the method comprising:
   (i) applying at least partial material removal of said at least one thin film of the structure to form a cross-section in the structure having a slope-like profile and thereby define measurement areas with different material thickness;
   (ii) sequentially performing optical measurements on at least some of said measurement areas, thereby obtaining measured data portions for said at least some of the measurement areas with different material thickness, respectively;
   (iii) determining the properties of said at least one thin film, by analyzing the measured data portion of the measurement area with minimal material thickness, and then sequentially interpreting the other measured data portions of the other measurement areas from the measured data portion of the measurement area with minimal material thickness towards the measured data portion of the measurement area with maximal material thickness, while utilizing for each measurement area the calculation results for the one or more measurement areas with smaller material thickness.

21. Method of optical measurements of thin film structures for determining the properties of at least one thin film, the method comprising:
   (i) applying at least partial material removal of said at least one thin film of the structure thereby forming measurement areas with different material thickness;
   (ii) sequentially performing optical measurements on at least some of said measurement areas starting from the measurement area with smaller material thickness, thereby obtaining measured data portions for said at least some of the measurement areas with different material thickness, respectively;
   (iii) determining the properties of said at least one thin film, by analyzing the measured data portion of the measurement area with minimal material thickness, and then sequentially interpreting the other measured data portions of the other measurement areas from the measured data portion of the measurement area with minimal material thickness towards the measured data portion of the measurement area with maximal material thickness, while utilizing for each measurement area the calculation results for the one or more measurement areas with smaller material thickness.

22. A system for use in measurements of thin film structures for determining the properties of at least one thin film, the system comprising:

(i) a material removal unit configured and operable for carrying out at least partial material removal of said at least one thin film of the structure so as to define measurement areas with different material thickness;

(ii) an optical unit configured and operable for performing optical measurements on at least some of the measurement areas, and generating measured data portions for said at least some of the measurement areas with different material thickness, respectively;

(iii) a data processor and analyzer connectable to the output of the optical unit for receiving and analyzing the measured data portions, the data processor and analyzer being configured for determining the properties of said at least one thin film, by analyzing the measured data portion of the measurement area with minimal material thickness, and then sequentially interpreting the other measured data portions of the other measurement areas from the measured data portion of the measurement area with minimal material thickness towards the measured data portion of the measurement area with maximal material thickness, while utilizing for each measurement area the calculation results for the one or more measurement areas with smaller material thickness.

23. The system according to claim 22, wherein said material removing unit comprises a polisher unit.

24. The system according to claim 23, wherein said polisher unit comprises a chemical mechanical polisher.

25. The system according to claim 22, wherein said material removing unit comprises etching unit.

26. The system according to claim 25, wherein said etching unit is configured to generate a focused ion beam.

27. The system according to claim 22, wherein said optical unit comprises at least one of the following: spectrophotometer, ellipsometer, FTIR unit, scatterometer.

28. The system according to claim 27, wherein the spectrophotometer is configured to produce polarized light.

29. The system according to claim 22, wherein the data processor and analyzer is configured for determining at least one of the following properties of the thin film: refractive index, extinction coefficient and layer thickness.

30. The system according to claim 29, wherein the data processor and analyzer is configured for determining the refractive index as a function of wavelength of incident light.

31. The system according to claim 29, wherein the data processor and analyzer is configured for determining the extinction coefficient as a function of wavelength of incident light.

32. The system according to claim 22, wherein said optical unit is configured for producing incident light of a wavelength range between DUV and NIR ranges.

33. The system according to claim 22, wherein the optical unit is configured for illuminating the measurement area by incident light and collecting light specularly reflected from the illuminated area.

* * * * *